United States Patent
Fan et al.

(10) Patent No.: US 11,497,402 B2
(45) Date of Patent: Nov. 15, 2022

(54) INTRAORAL OCT WITH COMPRESSIVE SENSING

(71) Applicant: Carestream Dental Technology Topco Limited, London (GB)

(72) Inventors: Chuanmao Fan, Rochester, NY (US); Victor C. Wong, Pittsford, NY (US)

(73) Assignee: Dental Imaging Technologies Corporation, Atlanta, GA (US)

( * ) Notice: Subject to any disclaimer, the term of this patent is extended or adjusted under 35 U.S.C. 154(b) by 0 days.

(21) Appl. No.: 16/092,098

(22) PCT Filed: May 16, 2016

(86) PCT No.: PCT/US2016/032659
§ 371 (c)(1),
(2) Date: Oct. 8, 2018

(87) PCT Pub. No.: WO2017/176300
PCT Pub. Date: Oct. 12, 2017

(65) Prior Publication Data
US 2019/0117076 A1   Apr. 25, 2019

Related U.S. Application Data

(60) Provisional application No. 62/318,788, filed on Apr. 6, 2016.

(51) Int. Cl.
*A61B 5/00* (2006.01)
*G06T 11/00* (2006.01)

(52) U.S. Cl.
CPC .......... *A61B 5/0066* (2013.01); *A61B 5/0088* (2013.01); *A61B 5/7232* (2013.01); *G06T 11/006* (2013.01); *A61B 5/0073* (2013.01); *A61B 5/0075* (2013.01);
(Continued)

(58) Field of Classification Search
CPC . G01B 9/02091; A61B 5/0066; A61B 5/0088; A61B 5/0073; A61B 5/0075; A61B 5/0077; A61B 5/7232
See application file for complete search history.

(56) References Cited

U.S. PATENT DOCUMENTS

| | | |
|---|---|---|
| 7,355,721 B2 | 4/2008 | Quadling et al. |
| 8,345,257 B2 | 1/2013 | Bonnema et al. |
| 8,345,261 B2 | 1/2013 | Quadling et al. |

(Continued)

OTHER PUBLICATIONS

Mei Young et al., "Real-time high-speed volumetric imaging using compressive sampling optical choerence tomography," Biomedical Optics Express, 2(9):2690-2697, (Aug. 2011).
(Continued)

*Primary Examiner* — Jonathan M Hansen
(74) *Attorney, Agent, or Firm* — Alston & Bird LLP

(57) ABSTRACT

A method for acquiring image data obtains, for an intraoral feature, optical coherence tomography (OCT) data in three dimensions wherein at least one dimension is pseudo-randomly or randomly sampled and reconstructs an image volume of the intraoral feature using compressive sensing, wherein data density of the reconstructed image volume is larger than that of the obtained OCT data in the at least one dimension or according to a corresponding transform. The method renders the reconstructed image volume for display.

20 Claims, 22 Drawing Sheets

(52) U.S. Cl.
CPC .......... *A61B 5/0077* (2013.01); *A61B 5/4547* (2013.01); *G06T 2207/10101* (2013.01)

(56) References Cited

U.S. PATENT DOCUMENTS

| | | | |
|---|---|---|---|
| 8,928,888 B2 | 1/2015 | Bonnema et al. | |
| 2010/0322497 A1* | 12/2010 | Dempsey | G01R 33/4826 |
| | | | 382/131 |
| 2013/0156283 A1* | 6/2013 | Beg | G01N 21/4795 |
| | | | 382/131 |
| 2013/0330686 A1 | 12/2013 | Kaji et al. | |
| 2014/0293289 A1* | 10/2014 | Reisman | G01B 9/02004 |
| | | | 356/479 |
| 2014/0340634 A1 | 11/2014 | Kuranov et al. | |
| 2015/0245770 A1 | 9/2015 | Liang et al. | |

OTHER PUBLICATIONS

WIPO Application No. PCT/US2016/032659, PCT International Preliminary Report on Patentability dated Oct. 9, 2018.
WIPO Application No. PCT/US2016/032659, PCT International Search Report dated Mar. 3, 2017.
WIPO Application No. PCT/US2016/032659, PCT Written Opinion of the International Searching Authority dated Mar. 3, 2017.

* cited by examiner $$f(x,y,z_0) \approx \frac{1}{(x_2-x_1)(y_2-y_1)} (f(Q_{11})(x_2-x)(y_2-y) + f(Q_{21})(x-x_1)(y_2-y) \\ + f(Q_{12})(x_2-x)(y-y_1) + f(Q_{22})(x-x_1)(y-y_1))$$

270

INTRAORAL OCT WITH COMPRESSIVE SENSING

FIELD OF THE INVENTION

The disclosure relates generally to methods and apparatus for optical coherence tomography imaging and more particularly to methods and apparatus for OCT using compressive sensing.

BACKGROUND OF THE INVENTION

Optical coherence tomography (OCT) is a non-invasive imaging technique that employs interferometric principles to obtain high resolution, cross-sectional tomographic images that characterize the depth structure of a sample. Particularly suitable for in vivo imaging of human tissue, OCT has shown its usefulness in a range of biomedical research and medical imaging applications, such as in ophthalmology, dermatology, oncology, and other fields, as well as in ear-nose-throat (ENT) and dental imaging.

OCT has been described as a type of "optical ultrasound", imaging reflected energy from within living tissue to obtain cross-sectional data. In an OCT imaging system, light from a wide-bandwidth source, such as a super luminescent diode (SLD) or other light source, is directed along two different optical paths: a reference arm of known length and a sample arm that illuminates the tissue or other subject under study. Reflected and back-scattered light from the reference and sample arms is then recombined in the OCT apparatus and interference effects are used to determine characteristics of the surface and near-surface underlying structure of the sample. Interference data can be acquired by rapidly scanning the sample illumination across the sample. At each of several thousand points, OCT apparatus obtains an interference profile which can be used to reconstruct an A-scan with an axial depth into the material that is a factor of light source coherence. For most tissue imaging applications, OCT uses broadband illumination sources and can provide image content at depths of a few millimeters (mm).

Initial OCT apparatus employed a time-domain (TD-OCT) architecture in which depth scanning is achieved by rapidly changing the length of the reference arm using some type of mechanical mechanism, such as a piezoelectric actuator, for example. TD-OCT methods use point-by-point scanning, requiring that the illumination probe be moved or scanned from one position to the next during the imaging session. More recent OCT apparatus can use a Fourier-domain architecture (FD-OCT) that discriminates reflections from different depths according to the optical frequencies of the signals they generate. FD-OCT methods simplify or eliminate axial scan requirements by collecting information from multiple depths simultaneously and offer improved acquisition rate and signal-to-noise ratio (SNR).

Because of their potential to achieve higher performance at lower cost, FD-OCT systems based on swept-frequency laser sources have attracted significant attention for medical applications that require subsurface imaging in highly scattering tissues. There are two implementations of Fourier-domain OCT: spectral domain OCT (SD-OCT) and swept-source OCT (SS-OCT).

SD-OCT imaging can be accomplished by illuminating the sample with a broadband illumination source and dispersing the reflected and scattered light with a spectrometer onto an array detector, such as a CCD (charge-coupled device) detector, for example. SS-OCT imaging illuminates the sample with a rapid wavelength-tuned laser and collects light reflected during a wavelength sweep using only a single photodetector or balanced photodetector. With both SD-OCT and SS-OCT, a profile of scattered light reflected from different depths is obtained by operating on the recorded interference signals using Fourier transforms, such as Fast-Fourier transforms (FFT), well known to those skilled in the signal analysis arts.

One of the challenges to SS-OCT is providing a suitable light source that can generate the needed sequence of wavelengths in rapid succession. To meet this need, swept-source OCT systems conventionally employ a high-speed wavelength sweeping laser that is equipped with an intracavity monochrometer or uses some type of external cavity narrowband wavelength scanning filter for tuning laser output. Examples of external devices that have been used for this purpose include a tunable Fabry-Perot filter whose cavity length is adjusted to provide a linear change of longitudinal mode, and a polygon scanner filter that selectively reflects dispersive wavelength light. Fourier domain mode locking is a recently reported technique that has been used to generate a sweeping frequency, generally most useful for OCT imaging using broadband near infrared (BNIR) wavelengths.

References for providing a tunable laser include the following:

S. R. Chinn, E. A. Swanson, and J. G. Fujimoto, "Optical coherence tomography using a frequency-tunable optical source," *Opt. Lett.* 22, 340-342 (1997);

B. Golubovic, B. E. Bouma, G. J. Tearney, and J. G. Fujimoto, "Optical frequency-domain reflectometry using rapid wavelength tuning of a Cr4+:forsterite laser," *Opt. Lett.* 22, 1704-1706 (1997);

S. H. Yun, C. Boudoux, G. J. Tearney, and B. E. Bouma, "High-speed wavelength-swept semiconductor laser with a polygon-scanner-based wavelength filter," *Opt. Lett.* 28, 1981-1983 (2003);

Woojin Shin, Boan-Ahn Yu, Yeung Lak Lee, Tae Jun Yu, Tae Joong Born, Young-Chul Noh, Jongmin Lee, and Do-Kyeong Ko, "Tunable Q-switched erbium-doped fiber laser based on digital micromirror array," *Opt. Express* 14, 5356-5364 (2006);

Xiao Chen, Bin-bin Yan, Fei-jun Song, Yi-quan Wang, Feng Xiao, and Kamal Alameh, "Diffraction of digital micro-mirror device gratings and its effect on properties of tunable fiber lasers," *Appl. Opt.* 51, 7214-7220 (2012).

Reference is also made to the following:

Huang, D; Swanson, E A; Lin, C P; Schuman, J S; Stinson, W G; Chang, W; Hee, M R; Flotte, T et al. (1991). "Optical coherence tomography". *Science* 254 (5035): 1178-81. Bibcode:1991Sci . . . 254.1178H. doi:10.1126/science.1957169.PMID 1957169;

U.S. Pat. No. 7,355,721 B2 entitled "Optical coherence tomography imaging" to Quadling et al.;

U.S. Pat. No. 8,345,261 B2 entitled "Optical coherence tomography imaging" to Quadling et al.;

U.S. Pat. Nos. 8,928,888 B2 and 8,345,257 B2, "Swept source optical coherence tomography (OCT) method and system", both to Bonnema et al.

U.S. Patent Application No. US20130330686A1 entitled " Dental optical measuring device and dental optical measuring/diagnosing tool" by Kaji et al.;

Hung, K.-W.; Siu, W.-C., "Fast image interpolation using the bilateral filter," in Image Processing, IET, vol. 6, no.7, pp. 877-890, October 2012. doi: 10.1049/iet-ipr.2011.0050;

D. L. Donoho, "Compressed Sensing," IEEE Trans. Inf. Theory 52(4), 1289-1306 (2006);

E. Candes, J. Romberg, and T. Tao, "Robust uncertainty principles: Exact signal reconstruction from highly incomplete frequency information," IEEE Trans. Inf. Theory 52(2), 489-509 (2006);

Foucart, Simon, and Holger Rauhut. A mathematical introduction to compressive sensing. Vol. 1. No. 3. Basel: Birkhäuser, 2013;

Evgeniy Lebed, Paul J. Mackenzie, Marinko V. Sarunic, and Faisal M. Beg, "Rapid Volumetric OCT Image Acquisition Using Compressive Sampling," Opt. Express 18, 21003-21012 (2010);

Xuan Liu and Jin U. Kang, "Compressive SD-OCT: the application of compressed sensing in spectral domain optical coherence tomography," Opt. Express 18, 22010-22019 (2010).

One aspect of OCT imaging that constrains its practical usability and effectiveness for medical and dental imaging applications relates to the speed of data acquisition. Because the OCT scan requires surface sampling at numerous points spaced along the surface, the scanner must be held stationary during the sampling period. Movement of the scanner probe while obtaining data can disrupt the sampling process and prevent or delay acquisition of sufficient and accurate data for surface reconstruction.

Thus, it can be appreciated that there is a need for improved scanning apparatus and methods for OCT imaging that can improve efficiency and that can help to make OCT more usable.

SUMMARY OF THE INVENTION

An aspect of this application is to advance the art of dental imaging systems.

Another aspect of this application is to address in whole or in part, at least the foregoing and other deficiencies in the related art.

It is another aspect of this application to provide in whole or in part, at least the advantages described herein.

It is an object of the present disclosure to advance the art of diagnostic imaging and to address the need for reducing the acquisition time needed for OCT scanning. An embodiment of the present invention provides apparatus and methods that can help to improve OCT sampling and leverage compressive sensing in both spatial and spectral domains.

These objects are given only by way of illustrative example, and such objects may be exemplary of one or more embodiments of the invention. Other desirable objectives and advantages inherently achieved by the disclosed methods may occur or become apparent to those skilled in the art. The invention is defined by the appended claims.

According to an aspect of the present disclosure, there is provided a method for acquiring image data comprising:

obtaining, for an intraoral feature, optical coherence tomography (OCT) data in three dimensions wherein at least one dimension is pseudo-randomly or randomly sampled;

reconstructing an image volume of the intraoral feature using compressive sensing wherein data density of the reconstructed image volume is larger than that of the obtained OCT data in the at least one dimension or according to a corresponding transform; and rendering the reconstructed image volume for display.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other. Some exaggeration may be necessary in order to emphasize basic structural relationships or principles of operation. Some conventional components that would be needed for implementation of the described embodiments, such as support components used for providing power, for packaging, and for mounting and protecting system optics, for example, are not shown in the drawings in order to simplify description.

DETAILED DESCRIPTION OF THE INVENTION

Figure 1:
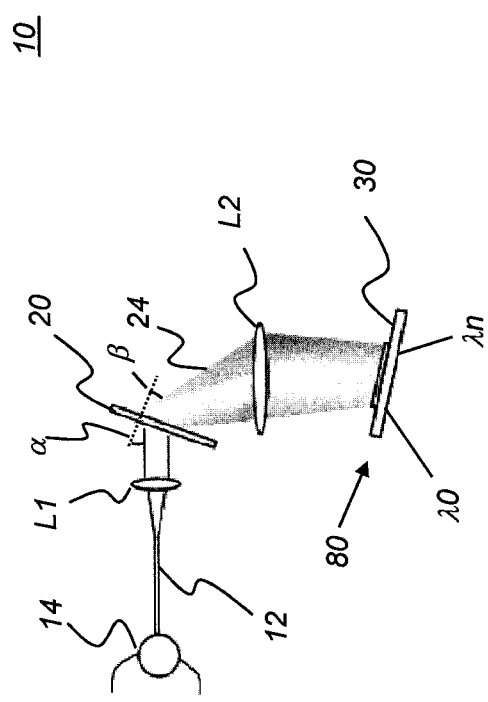
FIG. 1 is a schematic diagram that shows a programmable filter according to an embodiment of the present disclosure.

The following is a detailed description of exemplary embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the term "optics" is used generally to refer to lenses and other refractive, diffractive, and reflective components or apertures used for shaping and orienting a light beam. An individual component of this type is termed an optic.

In the context of the present disclosure, the terms "viewer", "operator", and "user" are considered to be equivalent and refer to the viewing practitioner, technician, or other person who may operate a camera or scanner and may also view and manipulate an image, such as a dental image, on a display monitor. An "operator instruction" or "viewer instruction" is obtained from explicit commands entered by the viewer, such as by clicking a button on the camera or scanner or by using a computer mouse or by touch screen or keyboard entry.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the term "camera" relates to a device that is enabled to acquire a reflectance, 2-D digital image from reflected visible or NIR light, such as structured light that is reflected from the surface of teeth and supporting structures.

The general term "scanner" relates to an optical sensor that projects a scanned light beam of broadband near-IR (BNIR) illumination that is directed to the tooth surface through a sample arm and acquired, as scattered light returned in the sample arm, for detecting interference with light from a reference arm used in OCT imaging of a surface. The term "raster scanner" relates to the combination of hardware components that scan light toward a sample, as described in more detail subsequently.

The term "subject" refers to the tooth or other portion of a patient that is being imaged and, in optical terms, can be considered equivalent to the "object" of the corresponding imaging system.

In the context of the present disclosure, the phrase "broadband light emitter" refers to an illumination or light source that emits a continuous spectrum output over a range of wavelengths at any given point of time. Short-coherence or low-coherence, broadband illumination sources can include, for example, super luminescent diodes, short-pulse lasers, many types of white-light sources, and supercontinuum light sources. Most low coherence length sources of these types have a coherence length on the order of tens of microns or less.

As is well-known to those skilled in the OCT imaging arts, the axial resolution is related to the coherence length of the light source. Thus, the shorter the coherence length, the higher the axial resolution.

Embodiments of the present disclosure can utilize any of the various types of OCT scanning methods, including time-domain or spectral or frequency-domain OCT. Because the speed advantage is of particular interest, the description that follows is primarily directed to embodiments that employ swept-source OCT, a type of frequency-domain OCT that is generally advantageous for faster speed and overall scanning throughput. However, it should be noted that the compressive sampling methods described in subsequent sections of this disclosure can be used to improve the response of time-domain OCT and other types of OCT as well as with SS-OCT. Methods of the present disclosure can also be used where a spectrometer is used for sensing in the OCT system.

According to an embodiment of the present disclosure, there is provided a programmable light source that can provide variable wavelength illumination that has advantages for improved OCT scanning methods as described herein. The programmable light source can be used as a swept-source for scanned SS-OCT and other applications that benefit from a controllably changeable spectral pattern.

Referring to FIG. 1, there is shown a programmable filter 10 that is used for generating a desired pattern and sequence of wavelengths ($\lambda 0 \ldots \lambda n$) from a low-coherence, broadband light source. Broadband light from a fiber laser or other source is directed, through a circulator 14 through an optical fiber or other waveguide 12 to a collimator lens L1 that directs the collimated light to a light dispersion optic 20, such as a diffraction grating. Light dispersion optic 20 forms a spectrally dispersed output beam 24, directed toward a focusing lens L2. Lens L2 focuses the dispersed light onto a spatial light modulator 80, such as a micro-mirror array 30. The micro-mirror array can be a linear array of reflective devices or a linear portion of a Digital Light Processor (DLP) from Texas Instruments, Dallas, Tex. One or more individual reflectors in array 30 is actuated to reflect light of corresponding wavelengths back through the optical path. This reflected light is the output of programmable filter 10 and can be used in applications such as optical coherence tomography (OCT) as described subsequently. Rapid actuation of each successive reflector in array 30 allows sampling of numerous small spectral portions of a spectrally dispersed output beam, such as that provided in FIG. 1. For example, where the spatial light modulator 80 is a micro-mirror array 30 that has 2048 micro-mirror elements in a single row, where the spectral range from one side of the array 30 to the other is 35 nm, each individual micro-mirror can reflect a wavelength band that is approximately 0.017 nm wide. One typical swept source sequence advances from lower to higher wavelengths by actuating a single spatial light modulator 80 pixel (reflective element) at a time, along the line formed by the spectrally dispersed output beam. Other swept source sequences are possible, as described subsequently.

Figure 2A:
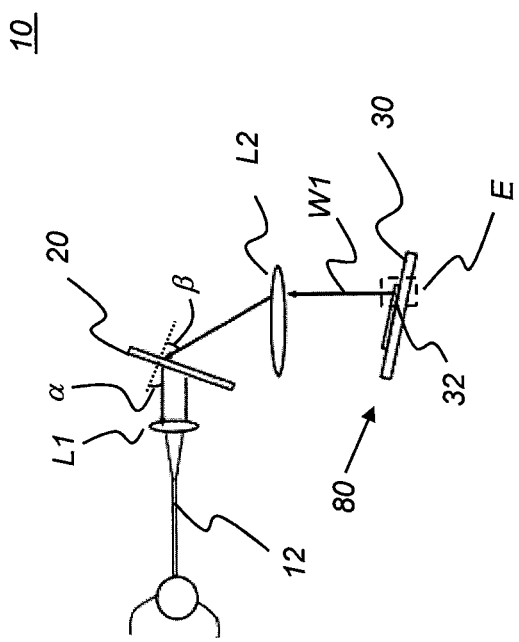
FIG. 2A is a simplified schematic diagram that shows how the programmable filter provides light of a selected wavelength band.
Figure 2B:
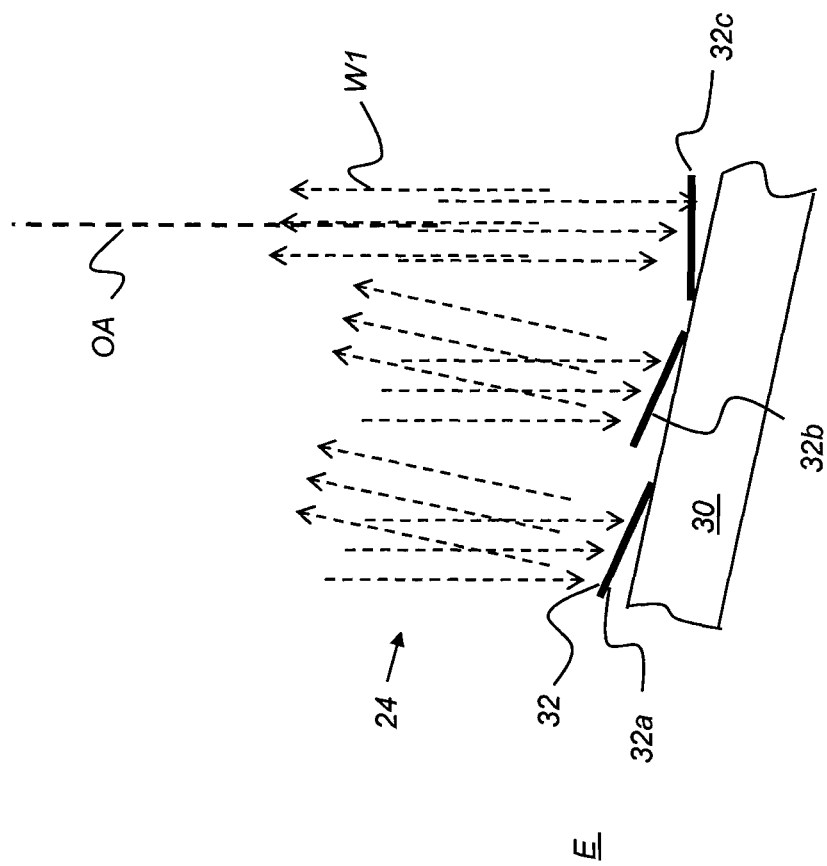
FIG. 2B is an enlarged view of a portion of the micromirror array of the programmable filter.
Figure 3:
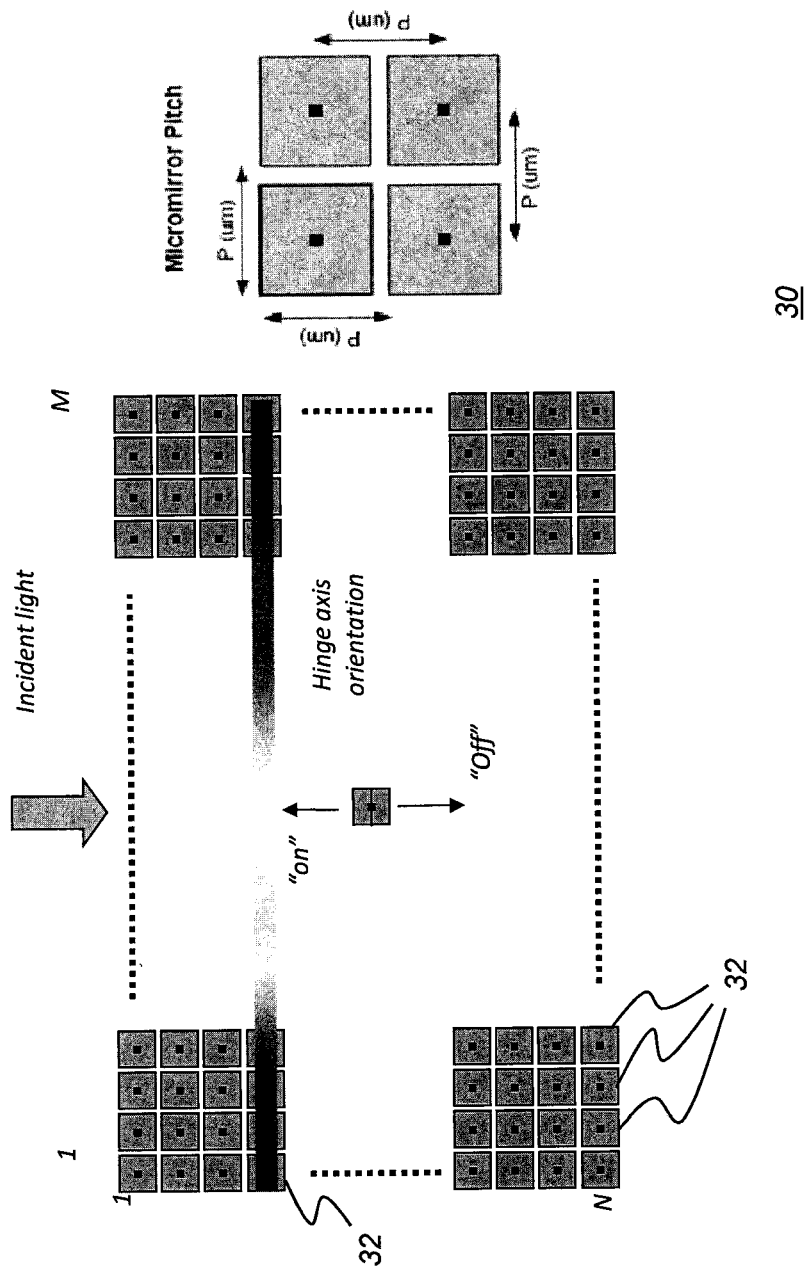
FIG. 3 is a plan view that shows the arrangement of micro-mirrors in the array.

The micro-mirror array 30 described herein and shown in FIGS. 1-3 and following is one type of possible spatial light modulator 80 that can be used as part of a programmable light source. The spatial light modulator 80 that is employed is a reflective device of some type, with discretely addressable elements that effectively provide the "pixels" of the device.

Programmable filter 10 resembles aspects of a spectrometer in its overall arrangement of components and in its light distribution. Incident broadband BNIR light is dispersed by light dispersion optic 20 in order to spatially separate the spectral components of the light. The micro-mirror array 30 or other type of spatial light modulator 80, as described in more detail subsequently, is disposed to reflect a selected wavelength band or bands of this light back through programmable filter 10 so that the selected wavelength band can be used elsewhere in the optical system, such as for use in an interferometry measurement device or for tuning a laser.

The simplified schematic of FIG. 2A and enlargement of FIG. 2B show how programmable filter 10 operates to provide light of a selected wavelength band W1. FIG. 2B, which schematically shows a greatly enlarged area E of micro-mirror array 30, shows the behavior of three mirrors 32a, 32b, and 32c with respect to incident light of beam 24. Each mirror 32 element of micro-mirror array 30 can have either of two states: deactuated, tilted at one angle, as shown at mirrors 32a and 32b; or actuated, tilted at an alternate angle as shown at mirror 32c. For DLP devices, the tilt angles for deactuated/actuated states of the micro-mirrors are +12 and −12 degrees from the substrate surface. Thus, in order to direct light back along optical axis OA through lens L2 and through the other components of programmable filter 10, micro-mirror array 30 is itself tilted at +12 degrees relative to the optical axis OA, as shown in FIG. 2B.

In the programmable filter 10 of FIG. 1, light dispersion optic 20 can be a diffraction grating of some type, including a holographic diffraction grating, for example. The grating dispersion equation is:

$$m\lambda = d(\sin \alpha + \sin \beta) \quad \text{(eq. 1)}$$

wherein:
λ is the optical wavelength;
d is the grating pitch;
α is the incident angle (see FIGS. 1, 2A), relative to a normal to the incident surface of optic 20;
β is the angle of diffracted light, relative to a normal to the exit surface of optic 20;
m is the diffraction order, generally m=1 with relation to embodiments of the present disclosure.

The FWHM (full-width half-maximum) bandwidth is determined by the spectral resolution of the grating $\delta\lambda_g$ and wavelength range on a pixel or micro-mirror 32 of the DLP device $\delta\lambda_{DLP}$, which are given as:

$$\delta\lambda_g = \lambda c \, d \cos \alpha / D \quad \text{(eq. 2)}$$

and $$\delta\lambda_{DLP} = dp \cos \beta / f \quad \text{(eq. 3)}$$

wherein:
D is the $1/e^2$ width of the incident Gaussian beam collimated by lens L1;
λc is the central wavelength;
d is the grating pitch;
p is the DLP pixel pitch, for each micro-mirror;
f is the focus length of focus lens L2.

The final FWHM bandwidth δλ is the maximum of ($\delta\lambda_g$, $\delta\lambda_{DLP}$). Bandwidth δλ defines the finest tunable wavelength range. For a suitable configuration for OCT imaging, the following relationship holds:

$$\delta\lambda_g \leq \delta\lambda_{DLP}.$$

In order to use the DLP to reflect the light back to the waveguide 12 fiber, the spectrally dispersed spectrum is focused on the DLP surface, aligned with the hinge axis of each micro-mirror 32. The DLP reference flat surface also tilts 12 degrees so that when a particular micro-mirror 32 is in an "on" state, the light is directly reflected back to the optical waveguide 12. When the micro-mirror is in an "on" state, the corresponding focused portion of the spectrum, with bandwidth corresponding to the spatial distribution of light incident on that micro-mirror, is reflected back to the waveguide 12 fiber along the same path of incident light, but traveling in the opposite direction. Circulator 14 in the fiber path guides the light of the selected spectrum to a third fiber as output. It can be readily appreciated that other types of spatial light modulator 80 may not require orientation at an oblique angle relative to the incident light beam, as was shown in the example of FIG. 2B.

The $1/e^2$ Gaussian beam intensity diameter focused on a single DLP pixel is as follows:

$$w = 4\lambda f/(\pi D \cos \beta/\cos \alpha) \quad \text{(eq. 4)}$$

Preferably, the following holds: w≤p. This sets the beam diameter w at less than the pixel pitch p. The maximum tuning range is determined by:

$$M \times \delta\lambda_{DLP},$$

wherein M is the number of DLP micro-mirrors in the horizontal direction, as represented in FIG. 3. As FIG. 3 shows, the array of micro-mirrors for micro-mirror array 30 has M columns and N rows. Only a single row of the DLP micro-mirror array is needed for use with programmable filter 10; the other rows above and below this single row may or may not be used.

The wavelength in terms of DLP pixels (micro-mirrors) can be described by the following grating equation:

$$\lambda_i = d\left(\sin \alpha + \sin\left(\tan^{-1}\left[\frac{p}{f}\left(\frac{N}{2} - i - 1\right)\right] + \beta\right)\right) \quad \text{(eq. 5)}$$

Wherein i is an index for the DLP column, corresponding to the particular wavelength, in the range between 0 and (M-1).

From the above equation (5), the center wavelength corresponding to each mirror in the row can be determined.

Figure 4:
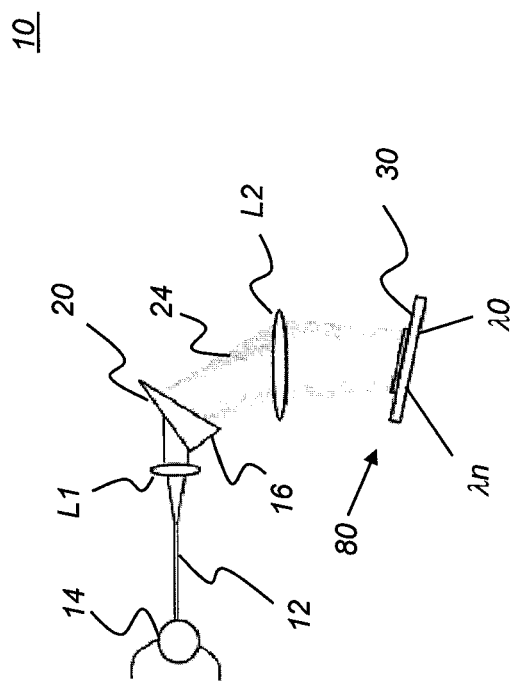
FIG. 4 is a schematic diagram that shows a programmable filter using a prism as its dispersion optic, according to an alternate embodiment of the present disclosure.

FIG. 4 shows programmable filter 10 in an alternate embodiment, with a prism 16 as light dispersion optic 20. The prism 16 disperses the light wavelengths (λn . . . λ0) in the opposite order from the grating shown in FIG. 1. Longer wavelengths (red) are dispersed at a higher angle, shorter wavelengths (blue) at lower angles.

Figure 5:
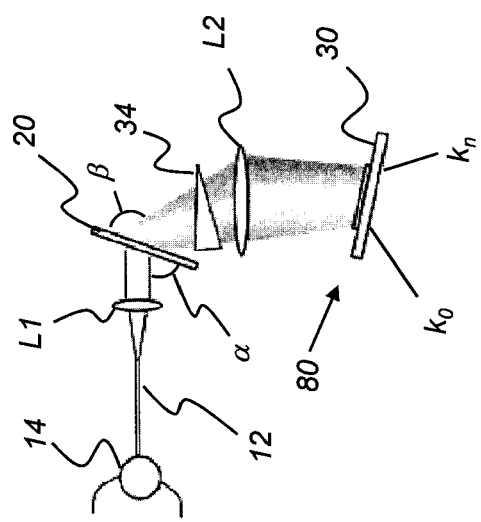
FIG. 5 is a schematic diagram showing a programmable filter that performs wavelength-to-wavenumber transformation, according to an alternate embodiment of the present disclosure.

Conventional light dispersion optics distribute the dispersed light so that its constituent wavelengths have a linear distribution. That is, the wavelengths are evenly spaced apart along the line of dispersed light. However, for Fourier domain OCT processing, conversion of wavelength data to frequency data is needed. Wavelength data (λ in units of nm) must thus be converted to wave-number data ($k = \lambda^{-1}$), proportional to frequency. In conventional practice, an interpolation step is used to achieve this transformation, prior to Fourier transform calculations. The interpolation step requires processing resources and time. However, it would be most advantageous to be able to select wave-number k values directly from the programmable filter. The schematic diagram of FIG. 5 shows one method for optical conversion of wavelength ($\lambda_0 \ldots \lambda_N$) data to wave-number ($k_0 \ldots k_N$) data using an intermediate prism 34. Methods for specifying prism angles and materials parameters for wavelength-to-wavenumber conversion are given, for example, in an article by Hu and Rollins entitled "Fourier domain optical coherence tomography with a linear-in-wavenumber spectrometer" in *OPTICS LETTERS*, Dec. 15, 2007, vol. 32 no. 24, pp. 3525-3527.

Programmable filter 10 is capable of providing selected light wavelengths from a broadband light source in a sequence that is appropriately timed for functions such as OCT imaging using a tuned laser. Because it offers a programmable sequence, the programmable filter 10 can perform a forward spectral sweep from lower to higher wavelengths as well as a backward sweep in the opposite direction, from higher to lower wavelengths. A triangular sweep pattern, generation of a "comb" of wavelengths, or arbitrary wavelength pattern can also be provided.

For OCT imaging in particular, various programmable sweep paradigms can be useful to extract moving objects in imaging, to improve sensitivity fall-off over depth, etc. The OCT signal sensitivity decreases with increasing depth into the sample, with depth considered to extend in the z-axis direction. Employing a comb of discrete wavelengths, for example, can increase OCT sensitivity. This is described in an article by Bajraszewski et al. entitled "Improved spectral optical coherence tomography using optical frequency comb" in *Optics Express*, Vol. 16 No. 6, March 2008, pp. 4163-4176.

Figure 6A:
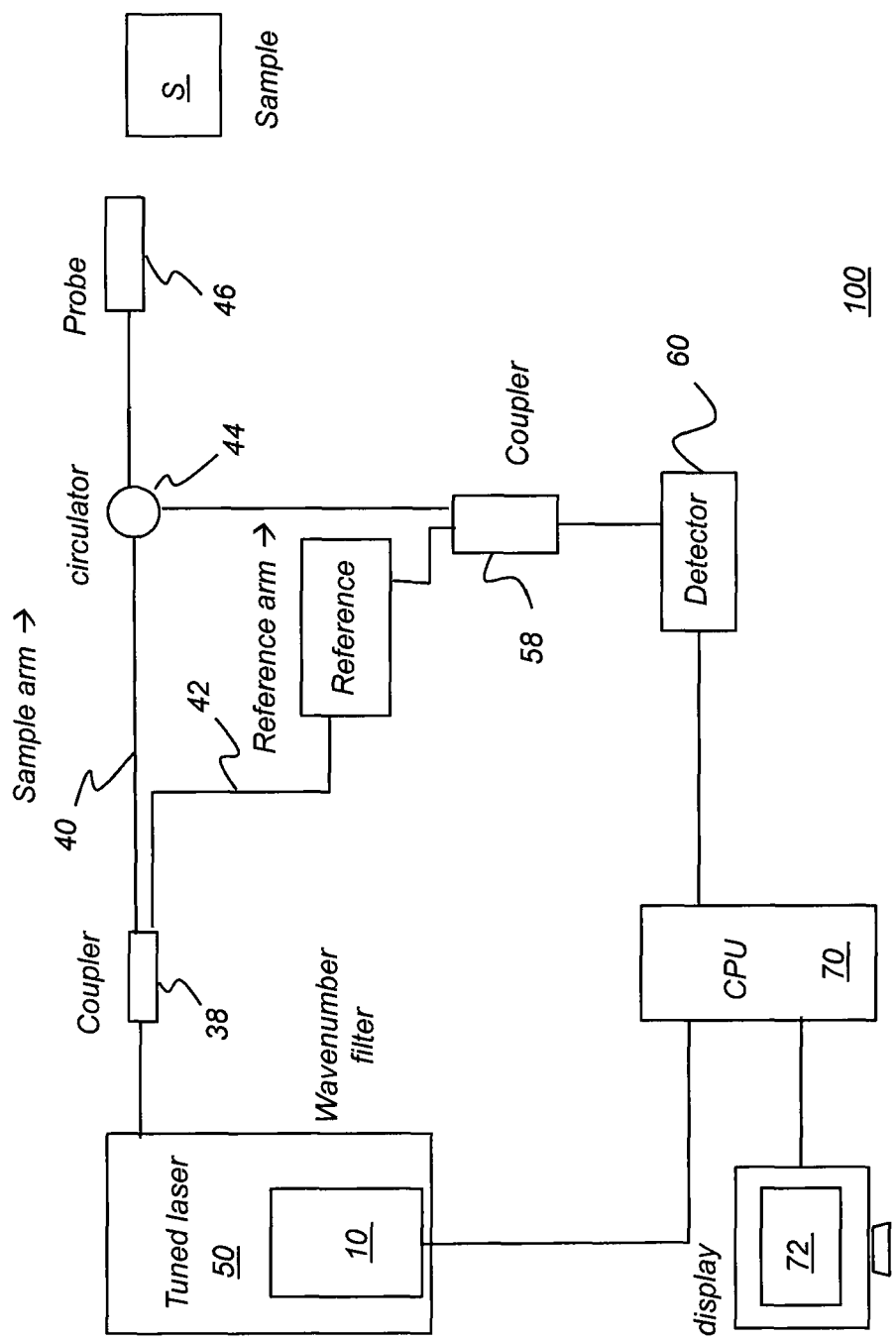
FIG. 6A is a schematic diagram showing a swept-source OCT (SS-OCT) apparatus using a programmable filter according to an embodiment of the present disclosure that uses a Mach-Zehnder interferometer.
Figure 6B:
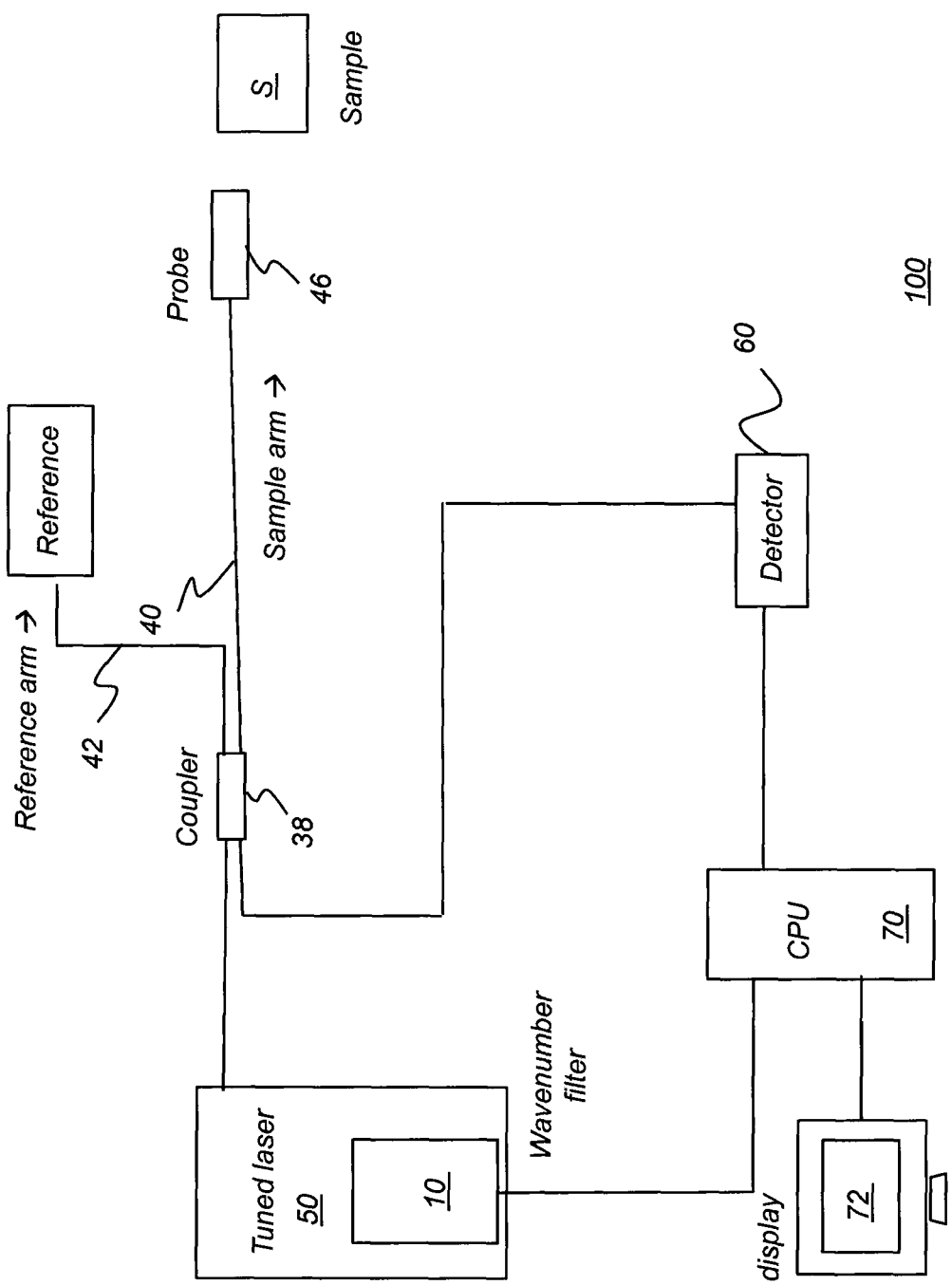
FIG. 6B is a schematic diagram showing a swept-source OCT (SS-OCT) apparatus using a programmable filter according to an embodiment of the present disclosure that uses a Michelson interferometer.

The simplified schematic diagrams of FIGS. 6A and 6B each show a swept-source OCT (SS-OCT) apparatus 100 using programmable filter 10 according to an embodiment of the present disclosure. In each case, programmable filter 10 is used as part of a tuned laser 50 that provides an illumination source. For intraoral OCT, for example, laser 50 can be tunable over a range of frequencies (wave-numbers k) corresponding to wavelengths between about 400 and 1600 nm. According to an embodiment of the present disclosure, a tunable range of 35 nm bandwidth centered about 830 nm is used for intraoral OCT.

In the FIG. 6A embodiment, a Mach-Zehnder interferometer system for OCT scanning is shown. FIG. 6B shows components for a Michelson interferometer system. For these embodiments, programmable filter 10 provides part of the laser cavity to generate tuned laser 50 output. The variable laser 50 output goes through a coupler 38 and to a sample arm 40 and a reference arm 42. In FIG. 6A, the sample arm 40 signal goes through a circulator 44 and to a probe 46 for measurement of a sample S. The sampled signal is directed back through circulator 44 (FIG. 6A) and to a detector 60 through a coupler 58. In FIG. 6B, the signal goes directly to sample arm 40 and reference arm 42; the sampled signal is directed back through coupler 38 and to detector 60. The detector 60 may use a pair of balanced photodetectors configured to cancel common mode noise. A control logic processor (control processing unit CPU) 70 is in signal communication with tuned laser 50 and its programmable filter 10 and with detector 60 and obtains and processes the output from detector 60. CPU 70 is also in signal communication with a display 72 for command entry and OCT results display.

Figure 7:
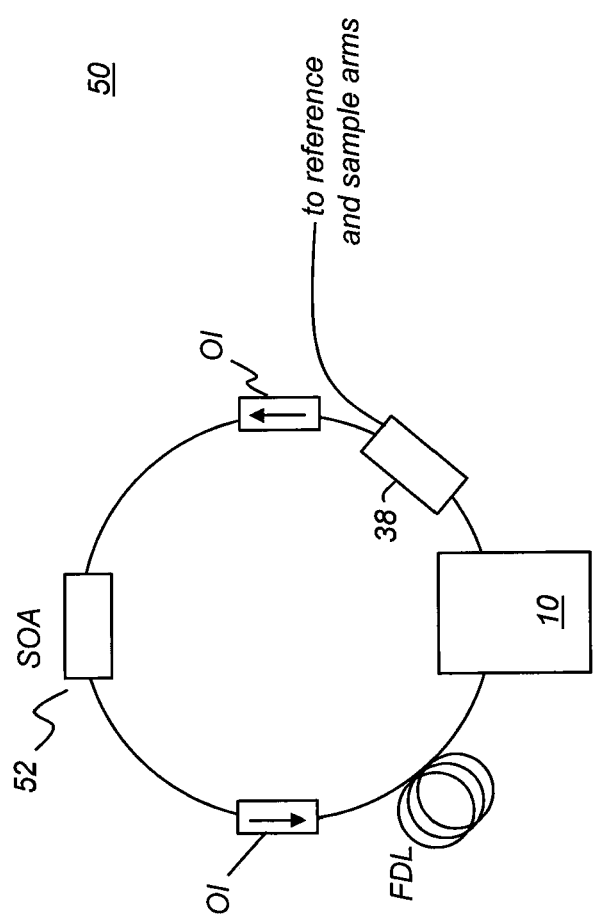
FIG. 7 is a schematic diagram that shows a tunable laser using a programmable filter according to an embodiment of the present disclosure.

The schematic diagram of FIG. 7 shows components of tuned laser 50 according to an alternate embodiment of the present disclosure. Tuned laser 50 is configured as a fiber ring laser having a broadband gain medium such as a semiconductor optical amplifier (SOA) 52. Two optical isolators OI provide protection of the SOA from back-reflected light. A fiber delay line (FDL) determines the effective sweep rate of the laser. Filter 10 has an input fiber and output fiber, used to connect the fiber ring.

Figure 8:
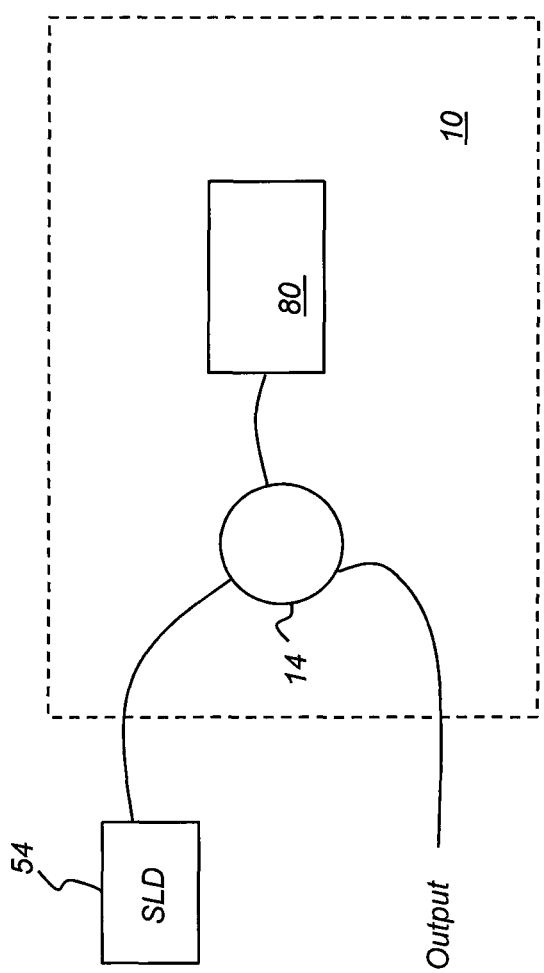
FIG. 8 is a schematic diagram that shows use of a programmable filter for selecting a wavelength band from a broadband light source.

The schematic diagram of FIG. 8 shows the use of programmable filter 10 for selecting a wavelength band from a broadband light source 54, such as a super luminescent diode (SLD). Here, spatial light modulator 80 reflects a component of the broadband light through circulator 14. Circulator 14 is used to direct light to and from the programmable filter 10 along separate optical paths.

Figure 9:
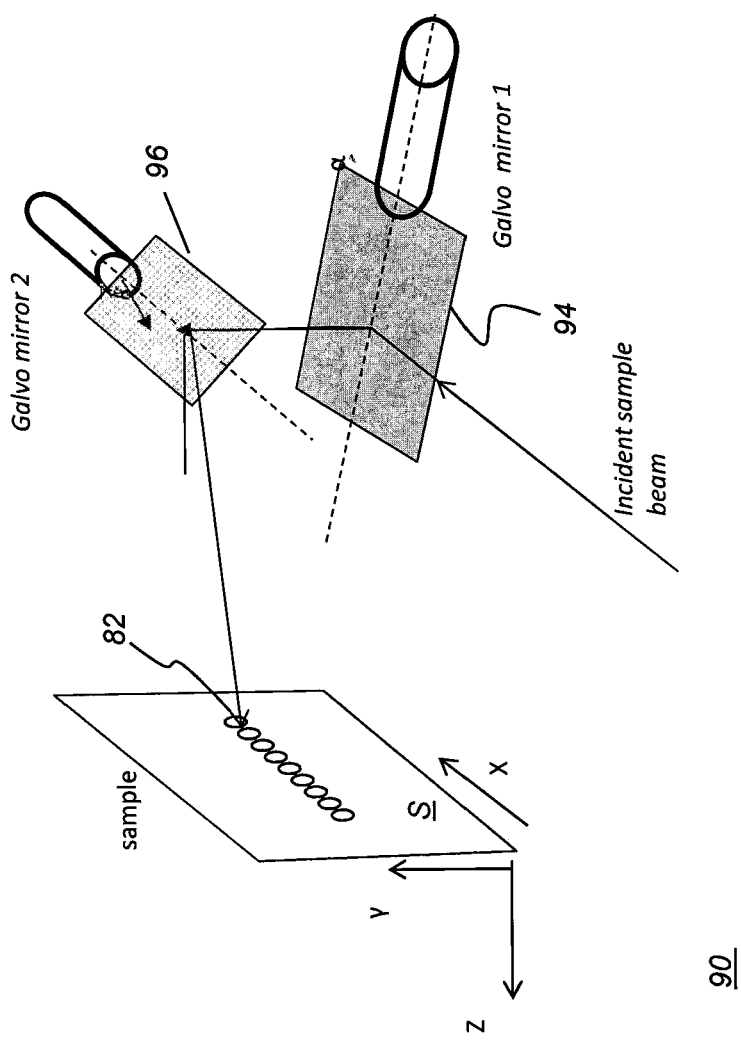
FIG. 9 shows galvo mirrors used to provide a 2-D scan as part of the OCT imaging system probe.

As shown in the schematic diagram of FIG. 9, galvo mirrors 94 and 96 cooperate to provide the raster scanning needed for OCT imaging. In the arrangement that is shown, galvo mirror 1 (94) scans the wavelengths of light to each point 82 along the sample to generate data along a row, which provides the B-scan, described in more detail subsequently. Galvo mirror 2 (96) progressively moves the row position to provide 2-D raster scanning to additional rows. At each point 82, the full spectrum of light provided using programmable filter 10, pixel by pixel of the spatial light modulator 80 (FIGS. 1, 4, 5), is rapidly generated in a single sweep and the resulting signal measured at detector 60 (FIGS. 6A, 6B).

Scanning Sequence for OCT Imaging

Figure 10A:
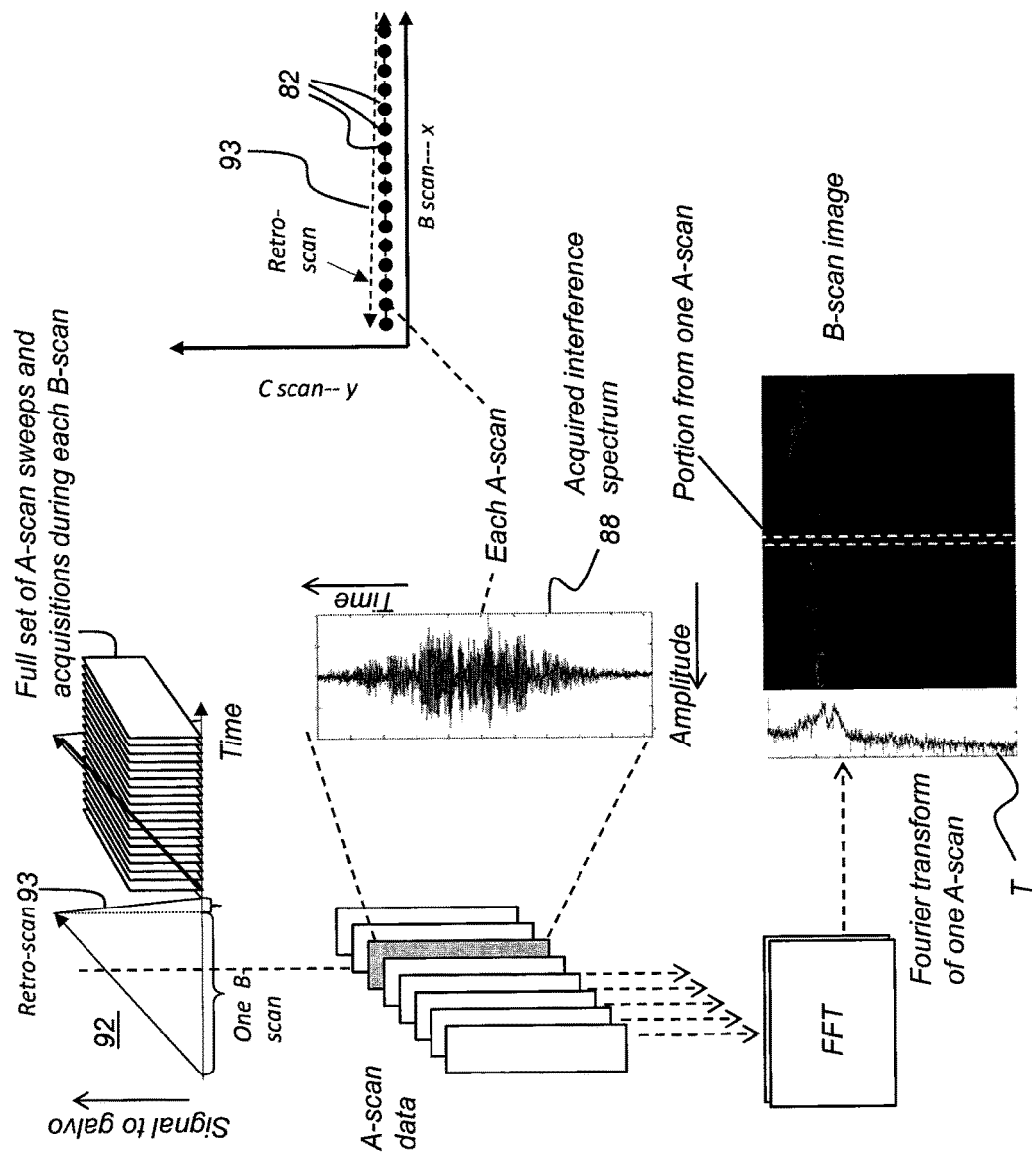
FIG. 10A shows a schematic representation of scanning operation for obtaining a B-scan.
Figure 10B:
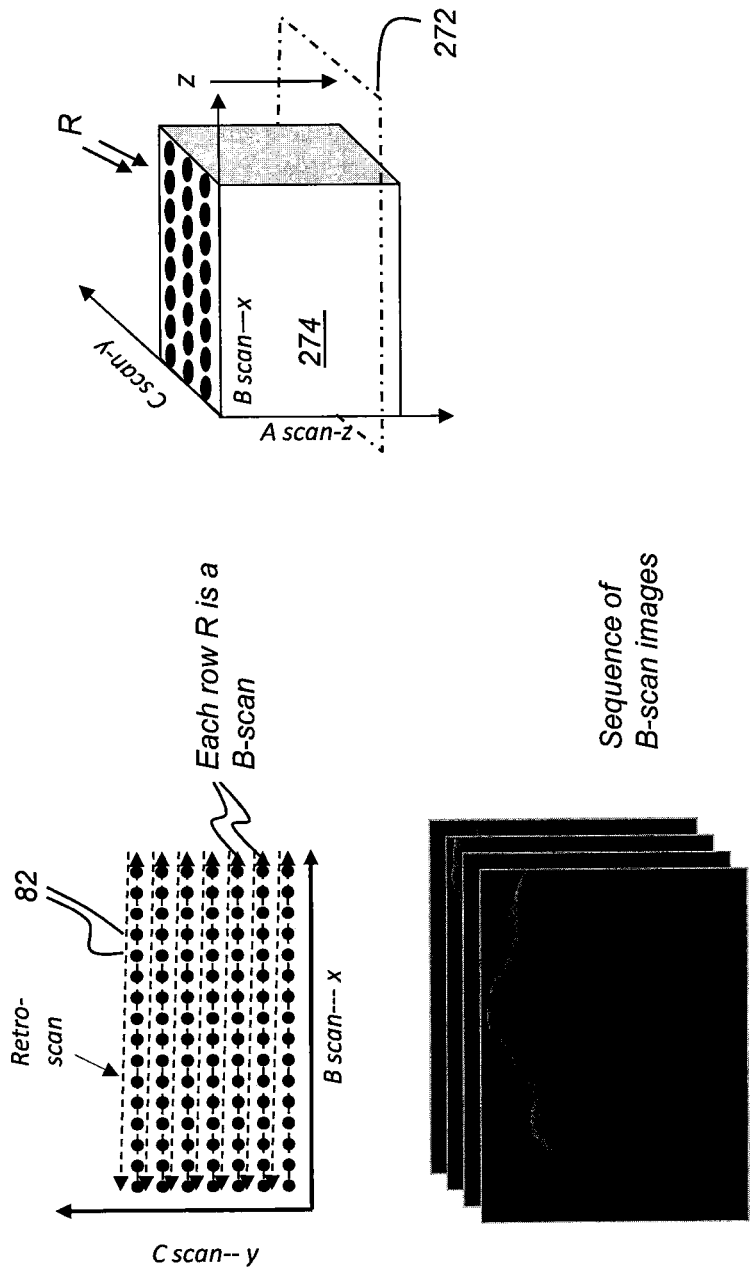
FIG. 10B shows an OCT scanning pattern for C-scan acquisition.

The schematic diagrams of FIGS. 10A and 10B show a scan sequence that can be used for forming tomographic images of an intraoral feature using the OCT apparatus of the present disclosure. The sequence shown in FIG. 10A shows how a single B-scan image is generated. A raster scanner 90 (FIG. 9) scans the selected light sequence as illumination over sample S, point by point. A periodic drive signal 92 as shown in FIG. 10A is used to drive the raster scanner 90 galvo mirrors to control a lateral scan or B-scan that extends across each row of the sample, shown as discrete points 82 extending in the horizontal direction in FIGS. 10A and 10B. At each of a plurality of points 82 along a line or row of the B-scan, an A-scan or depth scan, acquiring data in the z-axis direction, is generated using successive portions of the selected wavelength band. FIG. 10A shows drive signal 92 for generating a straightforward ascending sequence using raster scanner 90, with corresponding micro-mirror actuations, or other spatial light modulator pixel-by-pixel actuation, through the wavelength band. The retro-scan signal 93, part of drive signal 92, simply restores the scan mirror back to its starting position for the next line; no data is obtained during retro-scan signal 93.

It should be noted that the B-scan drive signal 92 drives the galvo mirror 94 for raster scanner 90 as shown in FIG. 9. At each incremental position, point 82 along the row of the B-scan, an A-scan is obtained. To acquire the A-scan data, tuned laser 50 or other programmable light source sweeps through the spectral sequence that is controlled by programmable filter 10 (FIGS. 1, 2A, 4, 5). Thus, in an embodiment in which programmable filter 10 causes the light source to sweep through a 30 nm range of wavelengths, this sequence for generating illumination is carried out at each point 82 along the B-scan path. As FIG. 10A shows, the set of A-scan acquisitions executes at each point 82, that is, at each position of the scanning galvo mirror 94. By way of example, where a DLP micro-mirror device is used as spatial light modulator 80, there can be 2048 measurements for generating the A-scan at each position 82.

FIG. 10A schematically shows the information acquired during each A-scan. An interference signal 88, shown with DC signal content removed, is acquired over the time interval for each point 82, wherein the signal is a function of the time interval required for the sweep, with the signal that is acquired indicative of the spectral interference fringes generated by combining the light from reference and feedback arms of the interferometer (FIGS. 6A, 6B). The Fourier transform generates a transform T for each A-scan. One transform signal corresponding to an A-scan is shown by way of example in FIG. 10A.

From the above description, it can be appreciated that a significant amount of data is acquired over a single B-scan sequence. In order to process this data efficiently, a Fast-Fourier Transform (FFT) is used, transforming the time-based signal data to corresponding frequency-based data from which image content can more readily be generated.

In Fourier domain OCT, the A scan corresponds to one line of spectrum acquisition which generates a line of depth (z-axis) resolved OCT signal. The B scan data generates a 2D OCT image as a row R along the corresponding scanned line.

Raster scanning is used to obtain multiple B-scan data by incrementing the raster scanner 90 acquisition in the C-scan direction. This is represented schematically in FIG. 10B, which shows how B-scan images can be represented and how 3-D volume information, a reconstruction 274, is generated using the A-, B-, and C-scan data.

As noted previously, the wavelength or frequency sweep sequence that is used for illumination at each A-scan point 82 can be modified from the ascending or descending wavelength sequence that is typically used. Arbitrary wavelength sequencing can alternately be used. In the case of arbitrary wavelength selection, which may be useful for some particular implementations of OCT, only a portion of the available wavelengths are provided as a result of each sweep. In arbitrary wavelength sequencing, each wavelength can be randomly selected, in arbitrary sequential order, to be used in the OCT system during a single sweep.

Figure 11:
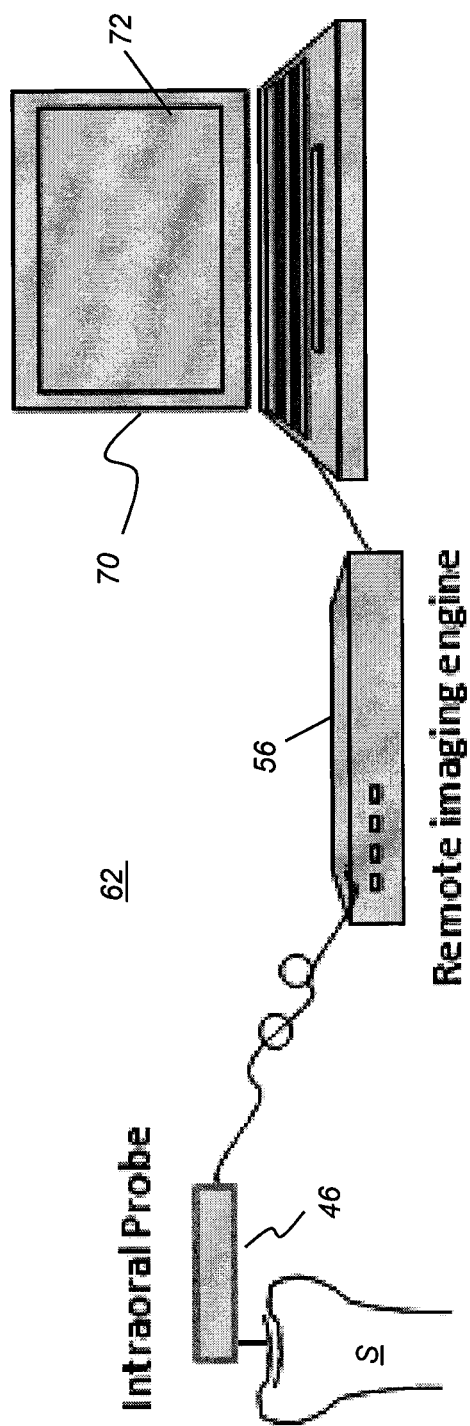
FIG. 11 is a schematic diagram that shows components of an intraoral OCT imaging system.

The schematic diagram of FIG. 11 shows probe 46 and support components for forming an intraoral OCT imaging system 62. An imaging engine 56 includes the light source, fiber coupler, reference arm, and OCT detector components described with reference to FIGS. 6A-7. Probe 46, in one embodiment, includes the raster scanner 90 or sample arm, but may optionally also contain other elements not provided by imaging engine 56. CPU 70 includes control logic and display 72.

The preceding description gives detailed description of OCT imaging system 62 using a DLP micro-mirror array 30 as one useful type of spatial light modulator that can be used for selecting a wavelength band from programmable filter 10. However, it should be noted that other types of spatial light modulator 80 could be used to reflect light of a selected wavelength band. A reflective liquid crystal device could alternately be used in place of DLP micro-mirror array 30, for example. Other types of MEMS (micro-electromechanical system devices) micro-minor array that are not DLP devices could alternately be used.

In the context of OCT imaging, an "en-face" image is a reconstructed image from an OCT scan that contains a single layer representation of the sample at a given depth. With respect to FIG. 10B, for example, a plane 272 indicates a depth level within a reconstructed OCT volume 274. The image that is obtained by representing the sample density data that lies along plane 272 is considered an en-face image. The en-face image need not be planar, however. An en-face image follows the surface contour of the sample, since each pixel that is used in the en-face image is an equivalent distance from the surface. An image formed using only the pixel on the surface of each scanned point would be a valid en-face image.

Certain exemplary method and/or apparatus embodiments can provide for dental OCT scan acquisition using compressive sampling. According to an embodiment of the present disclosure, there is provided an apparatus and method for OCT scan acquisition using compressive sampling methods that offer improved speed over conventional OCT scan patterns, without compromising the accuracy of surface information that is obtained. As is known to those skilled in the signal acquisition and analysis arts, compressive sampling techniques are characterized by (i) a randomized sampling of the measured data and can be employed when (ii) the sampled data has a sparse representation in some domain.

Figure 12A:
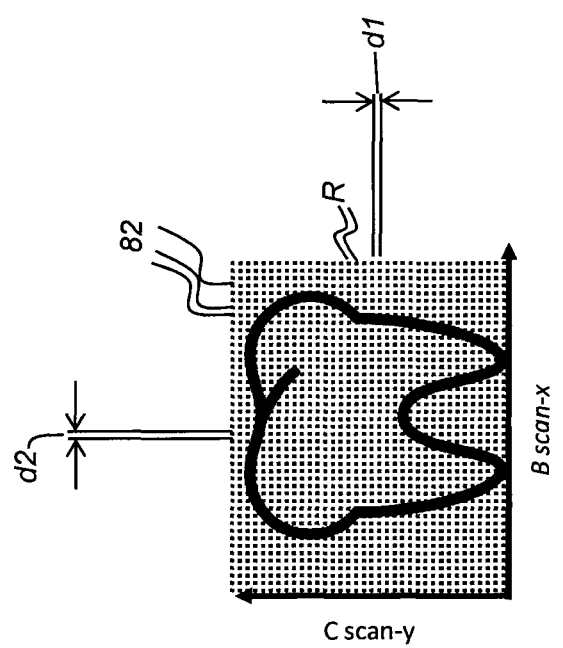
FIG. 12A is a schematic diagram that shows an OCT sampling pattern with equal spacing between samples.

The schematic diagram of FIG. 12A shows an OCT sampling pattern that employs standard, equal spacing between A-scans and between rows of A-scans. The A-scan locations at points 82 along the imaged surface are evenly spaced apart, between rows R as shown by a spacing d1 and within rows, as shown by a spacing d2, which may or may not equal point 82 spacing d1. This dense sampling enables close approximation of near-surface characteristics, but requires performing a considerable number of A-scans, with the accompanying requirements to store and process this dense data.

In spite of the improved speeds available using frequency-domain OCT scanning, however, the scan process takes time and may provide only a few volumes of OCT data frames per second (fps). At slower rates, problems such as unintended patient or probe movement can complicate and delay the OCT scan and can adversely affect the quality of scan results.

Figures 12B, 12C:
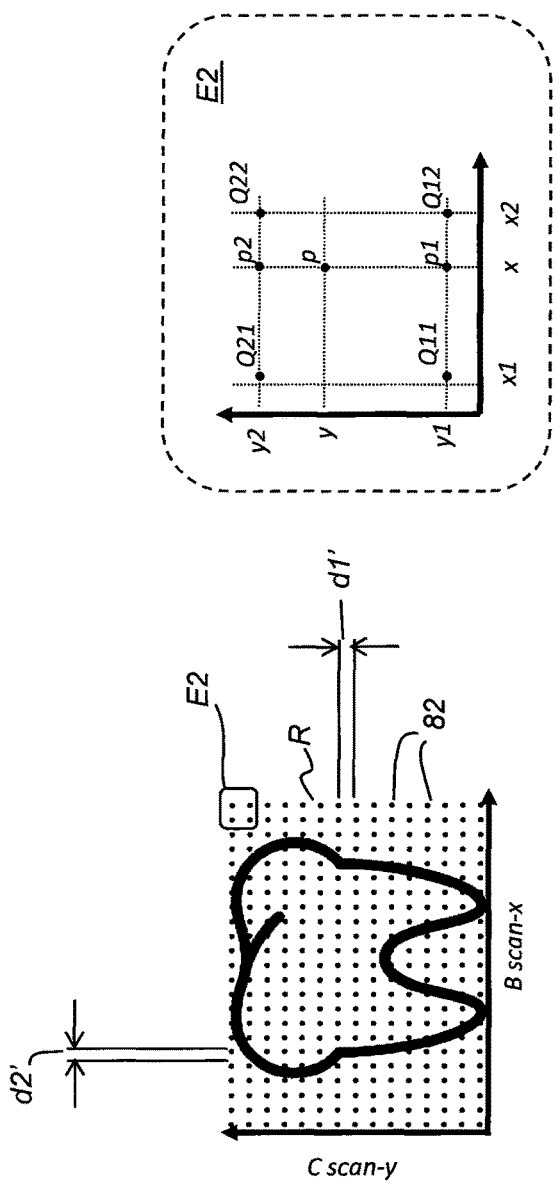
FIG. 12B is a schematic diagram that shows an OCT sampling pattern with increased spacing between samples.
FIG. 12C shows an equation for bilinear interpolation that can be used with the scanning arrangement of FIG. 12B.

One approach to reducing the time requirement for OCT scanning of a surface and effectively increasing the frames per second (fps) rate is to use an interpolation method, such as bilinear or trilinear interpolation, for example. The use of bilinear interpolation, shown schematically for a small area of the measured sample in FIG. 12B, enables a corresponding reduction in scan density with minimal loss of information. According to an embodiment of the present disclosure, the sample volume is reconstructed using reduced-density scan readings, with increased spacing d1' and d2' between rows and columns (spacing between points 82 in a row R), respectively. Then the missing OCT data can be recovered layer by layer (in the z-direction as shown in FIG. 10B) as each en-face display of the sample is generated. Thus, for a given layer $z_n$, the x- and y-values between scan values can be computed using interpolation methods such as the bilinear interpolation using a calculation such as that provided by an equation 270. For the FIG. 12B enlargement E2, values Q11, Q12, Q21, Q22 are actual measured values at coordinates (x1, y1), (x2, y1), (x1, y2), and (x2, y2) respectively. The missing value at p in layer $z_0$, for the example shown in enlarged portion E2, is $f(x, y, z_0)$ as shown in the calculation of FIG. 12C.

Compressive sensing is an emerging sampling approach, used in electronic signal analysis for example, that recovers a signal from randomly sampled data that would otherwise seem to be able to provide only incomplete information. Compressive sensing has been used in a range of signal processing applications, including magnetic resonance imaging (MRI), Radar, single pixel imaging, photoacoustic imaging, and OCT. The underlying theory for compressive sensing states that if a signal has a sparse representation in an orthonormal space/system such as Fourier transform space, wavelet transform space, or cosine transform space, for example, the signal can be recovered from randomly sparsely sampled signals by minimizing the $l_1$ norm, subject to certain constraints:

$$\text{Min}\|z\|_1, \text{ subject to } \|Az-y\|_2 \leq \varepsilon,$$

wherein $\|.\|_1$ is the $l_1$ norm and z is the signal to be constructed, y is the sparse sampling, A is the random sampling matrix such as a Gaussian or Bernoulli matrix. Sampling problems that can be transformed to this standard format can use sparse sampling and corresponding algorithms to recover the signal z with controlled error. This sampling theory seemingly violates the conventional, intuitive rules of signal acquisition and reconstruction that follow the basic principles of Nyquist sampling theory. The feasibility of compressive sampling relies on the fact that the true signal can be well represented by a sparse expansion of a suitable orthonormal basis. Compressive sensing and representation can be employed in image processing of under-sampled signals; similar insight is behind a number of forms of image compression, such as for the familiar JPEG (Joint Photographic Experts Group), JPEG2000, and related image data formats.

The OCT volume (x,y,k), where x and y are the spatial probing positions and k is the wavenumber, has sparse representation in wavelet space for spatial dimensions x,y and in Fourier transform space for k. Thus, compressive sampling is applicable to OCT imaging. When applied to OCT sensing, the compressive sampling/probing must be in a randomized manner and can be applied in one dimension, two dimensions, or three dimensions. High fidelity images can be efficiently reconstructed by solving the quadratically constrained $l_1$ norm minimization problem. This can substantially reduce the data acquisition time, which is desirable for intraoral OCT scanning.

However, truly random sampling positions are not practical in OCT scanning, due, at least in part, to hardware considerations. Instead, a pseudo random sequence is used. The feasibility of sparse sampling, more properly termed compressive sampling, relies on the fact that the true signal, provided that it can be considered sparse with respect to some vector domain, can be well represented by a sparse expansion of a suitable basis. This allows representation and storage of sizable image data with a fraction of the storage required for more conventional image representation schemes. For OCT scanning as used herein, the approximated OCT scan signal can be recovered using compressive sensing.

The schematic diagram of FIG. 13 shows, again viewing from the x-y plane, a scan sampling arrangement that can be used with a compressive sensing reconstruction according to one embodiment of the present invention. Here, either or both row spacing d1' and inter-sample spacing d2' of A-scans corresponding to points 82 along each row R can be randomly distributed, not only allowing spacing d1' and d2' to be further apart than in the dense distribution shown in FIG. 12A, but also allowing the spacing distances for either or both d1' and d2' to be varied, between rows and within rows, respectively. Thus, for example, points 82 along a row R can have unequal spacing or randomized spacing, so that some points 82 are closer to adjacent points 82 along the row R than are others. Similarly, some rows R can be more densely spaced from adjacent rows than are others.

Figure 13:
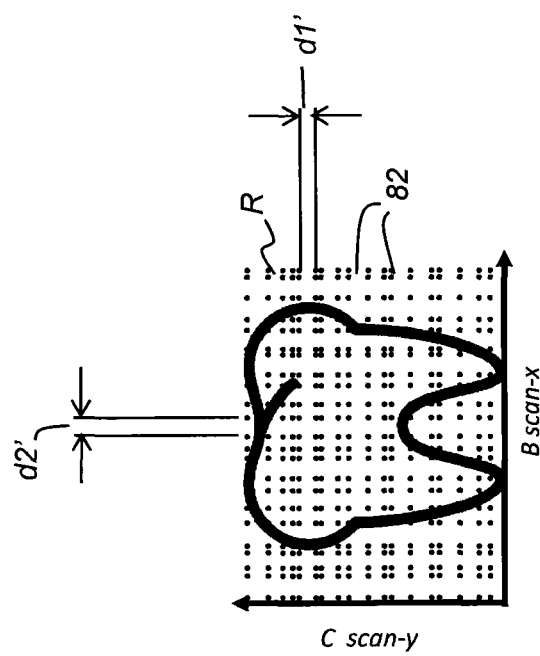
FIG. 13 is a schematic diagram that shows an OCT sampling pattern that uses a somewhat randomized arrangement.

FIG. 13 represents a randomized sampling OCT in two spatial dimensions, x and y. Here, in an arrangement with irregular sample spacing, x scan positions are generated from first a pseudo-random sequence. The y scan positions are then determined using a second pseudo-random sequence. The 2D sampling grid can be determined by interleaving the x and y sequences. The sampling tuples ($x_i$, $y_i$) are created from $x_i$ components of x random sampling sequence $x=\{x_1, x_2, \ldots x_W\}$ and $y_i$ components of y random sampling sequence $y=\{y_1, y_2, \ldots, y_D\}$. This forms a randomized, or pseudo-random spacing arrangement that can help to reduce the number of samples that need to be obtained for generating an OCT reconstruction.

Figure 14:
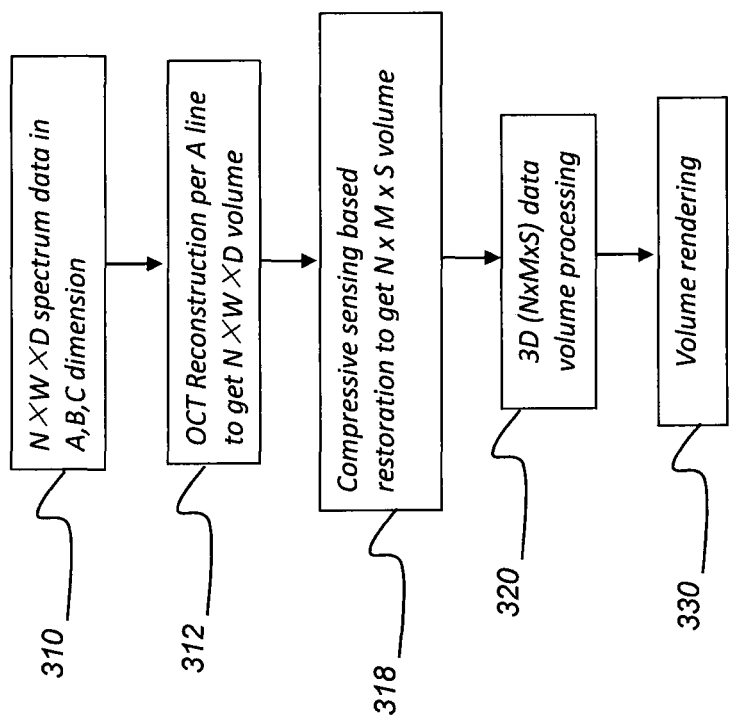
FIG. 14 is a logic flow diagram that shows a sequence for reconstruction of the sampled volume for spatial randomized sampled data, such as using the sampling arrangement described with reference to FIG. 13.

The logic flow diagram of FIG. 14 shows a sequence for reconstruction of the sampled volume for spatially random-sampled data, such as using the sampling arrangement described with reference to FIG. 13. An acquisition step 310 obtains the spectral data results for the OCT scan, with a dense depth value N for A-scans in each row, a randomized subsampled row width W for each row B and randomized subsampled D rows, providing the A, B, C dimension data represented in preceding figures. A reconstruction step 312 then performs conventional OCT reconstruction using each A-scan data to generate the depth resolved tomographic signal from each A scan. Then, a compressive-sensing-based restoration 318 fills in the data, providing M row width with S rows of tomographic data points to provide full resolution with respect to B and C dimensions, where M>W, and S>D. Compressive-sensing-based restoration step 318 can be accomplished by carrying out a nonlinear optimization using methods well-known to those skilled in the art, such as the iterative soft thresholding method. An optional volume processing step 320 can provide filtering, segmentation, and cropping. A volume rendering step 330 then allows display of the generated reconstruction. The reconstructed volume data can be stored and transmitted with or without volume processing and/or rendering.

The embodiment described in relation to FIGS. 13 and 14 provides for compressive sensing and reconstruction in two spatial dimensions. Depending on the imaging configurations and requirements, it may be preferred to perform randomized sampling in one spatial dimension and dense sampling in the other spatial dimension. In such cases, compressive sensing and reconstruction can just be done in one spatial dimension in the same way described above.

As noted previously, compressive sensing (CS) techniques require (i) some type of randomized sampling and (ii) sparsity with respect to signal representation. A signal can be considered "sparse" provided that the signal can be represented in some domain using only a few nonzero coefficients. For spectral-domain OCT, the spectral data for depth resolution can be sparsely represented in its Fourier domain, while the spatial data can be more conveniently represented as sparse in other domains such as wavelet domain. Because it can be configured to meet requirements for randomized sampling and sparse representation, OCT reconstruction of an A-scan also allows the use of compressive sensing techniques.

An embodiment of the present disclosure can use compressive sensing techniques for data in three dimensions: two spatial (sample spacing x, y) dimensions and one spectral (depth) dimension to obtain a sequence of spectral frequencies (wavelengths) that acquire the A-scan data at each scanned point 82. Compressive sensing in the depth direction for A-scan data can employ sparse data representation in the Fourier domain. Compressive sensing for spatial sampling can employ sparse data representation in the wavelet domain, for example.

As previously described with reference to spatial light modulator 80 and programmable filter 10 (FIGS. 1-5), the light source used for OCT scanning can be programmed with instructions to provide an arbitrary wavelength pattern. That is, for OCT sensing, the full swept-source sequence with continuously increasing or decreasing wavenumbers (wavelengths) is not needed. Instead, a sequence of discrete, randomized frequencies can be used for the OCT scan, obtaining sparsely represented measured data that can then be suitably processed using compressive sensing techniques.

Figures 15A, 15B:
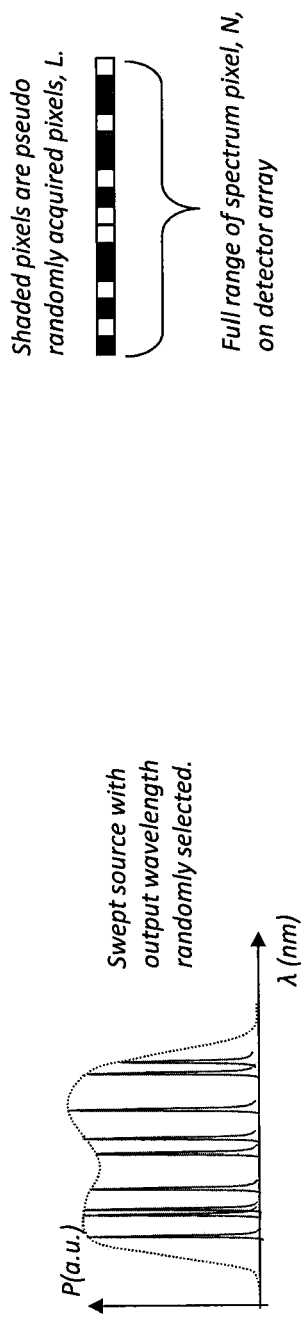
FIGS. 15A and 15B are schematic diagrams that show the use of sparse spectral content for OCT acquisition.

FIGS. 15A and 15B are schematic diagrams that show the use of randomized sparse spectral content for OCT acquisition. N pixels can be obtained in a single A-scan using the full spectral range. Instead of using the full range, a discrete, randomized set of frequencies (wavelengths) is used for the A-scan, reducing the number of pixels acquired. The graph in FIG. 15A, mapping wavelengths λ to arbitrary power units for signal intensity, represents the smaller set of discrete, pseudo-randomized frequencies (wavelengths) used in a single A-scan in a swept source OCT system. The same set of frequencies is used in each A-scan. In a spectral domain OCT system, randomized spectral sampling is achieved by obtaining the signal from pseudo-randomly selected pixels on the detector array, as shown in FIG. 15B.

Figure 15C:
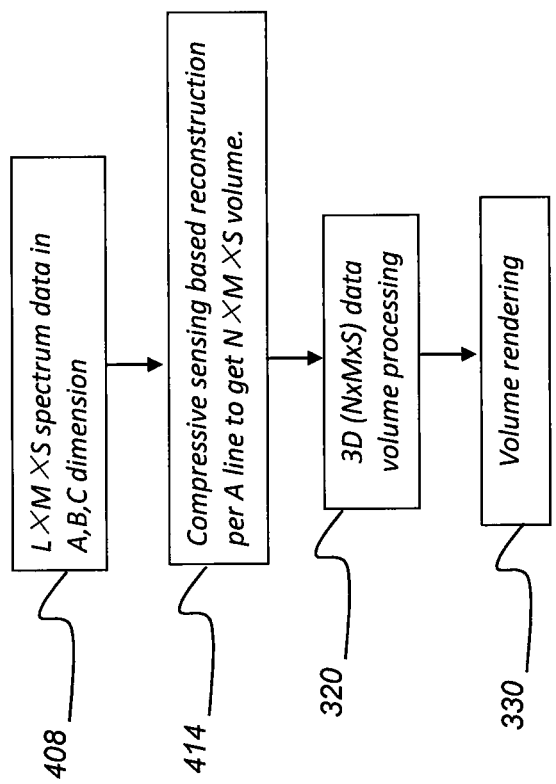
FIG. 15C is a logic flow diagram that shows a sequence for reconstruction of the sampled volume for data that is sparsely sampled only in the spectral dimension.

The logic flow diagram of FIG. 15C shows a sequence for reconstruction of the sampled volume for data that is randomly sampled and sparsely represented only with respect to the spectral dimension, such as using the sampling arrangement described with reference to FIGS. 15A and 15B. An acquisition step 408 obtains the spectral data results for the OCT scan, with a randomized subsampled depth value L for A-scans in each row, a dense row width M for each row B, and S dense rows, providing the A, B, C dimension data represented in preceding figures. A compressive-sensing-based reconstruction 414 fills in the data in the depth dimension, providing N depth values per A line, using methods well-known in the arts, such as the iterative conjugate gradients method. This step generates the depth resolved tomographic signal from each A scan, providing a full resolution (N×M×S) OCT image data volume of the scanned intraoral feature or other subject.; where N>L. An optional volume processing step 320 can provide filtering, segmentation, and cropping. A volume rendering step 330 then allows storage, transmission, and display of the generated reconstruction, such as rendering a two-dimensional image of the reconstructed volume for a tooth or other intraoral feature.

Figure 16:
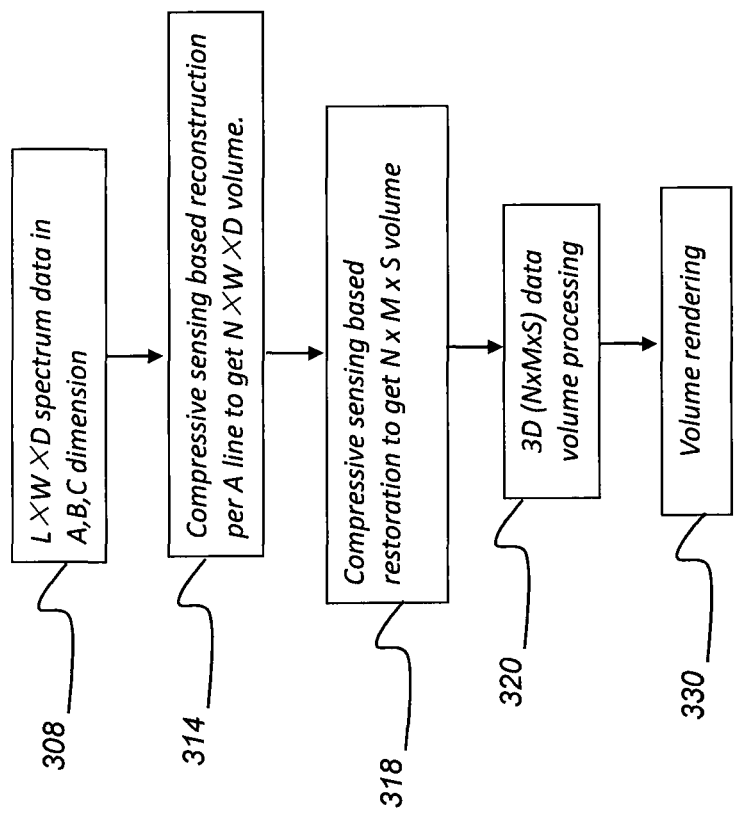
FIG. 16 is a logic flow diagram that shows a sequence for reconstruction of the sampled volume for spatial randomly sampled data, including the third added dimension using randomly sampled spectral scan content.

The logic flow diagram of FIG. 16 shows a sequence for reconstruction of the sampled volume for randomized or pseudo-random spatially sampled data, in both x, y (row, column) spatial dimensions and including the third added dimension using randomly sampled spectral scan content. An acquisition step 308, obtains the spectral data results for the OCT scan, with a randomized subsampled number L of spectral data points for A-scan depth, a randomized subsampled number W A-scans per row, and a randomized subsampled number D rows, providing the A, B, C dimension data represented in preceding figures. A compressive-sensing-based reconstruction step 314 fills in the data in each depth profile, providing N full-resolution depth values in the A dimension, as described with reference to FIG. 15C. This generates an N×W×D volume of depth-resolved tomographic signal. Then another compressive-sensing-based restoration step 318 is performed, filling in the data in the B and C dimensions to provide full-resolution (N×M×S) OCT image volume. This expands the set of OCT data that can be further conditioned in optional volume processing step 320. A volume rendering step 330 then allows storage, transmission, and display of the generated reconstruction. Data density of the reconstructed image volume is larger than that of the acquired OCT data, where N>L, M>W, and S>D.

Alternately, compressive-sensing-based restoration step 318 in the B and C spatial dimensions can be performed after data acquisition step 308 to get L×M×S volume first, then followed by compressive-sensing-based reconstruction step 314 in the A dimension to obtain full resolution (N×M×S) OCT image volume.

FIG. 16 is described in relation to reconstruction of the sampled volume for randomly sampled data in one spectral dimension and two spatial dimensions. OCT image volume reconstruction can be similarly done for sparsely sampled data in the spectral dimension and one spatial dimension.

Figure 17:
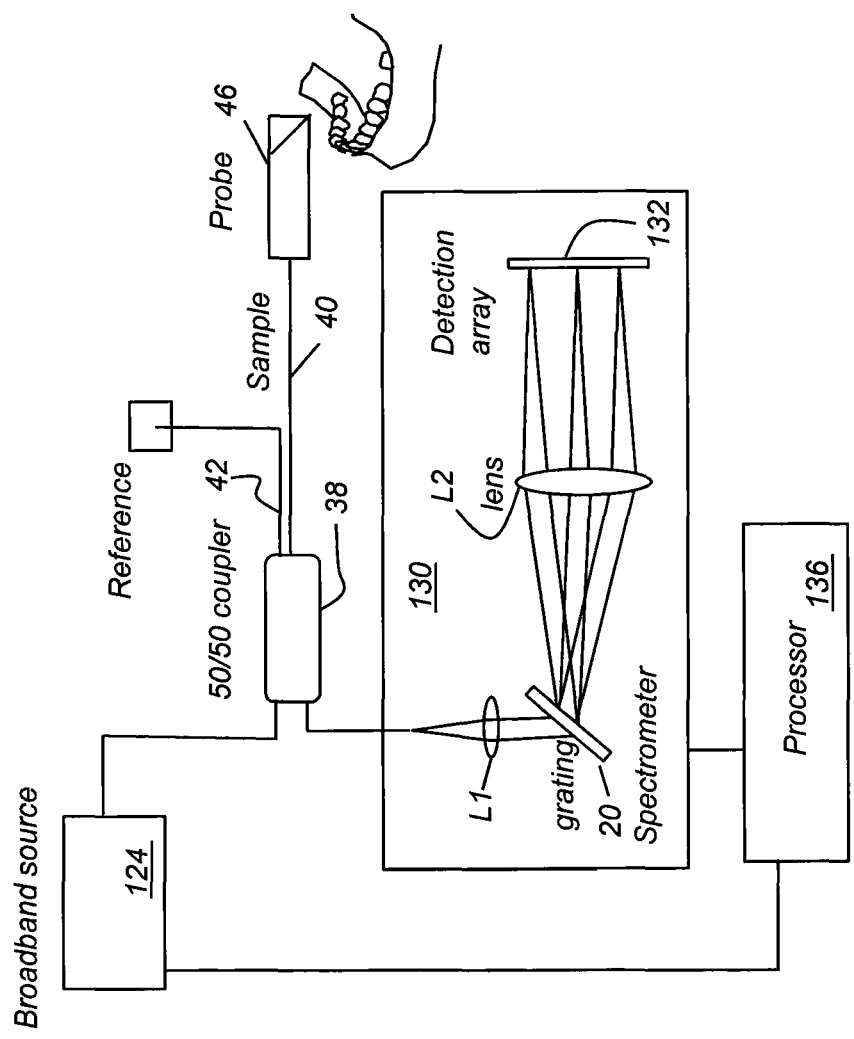
FIG. 17 is a schematic diagram showing an apparatus for compressive sampling using a spectrometer.

FIG. 17 is a schematic diagram showing an OCT apparatus for compressive sampling using a spectrometer 130 in a spectral domain (SD) OCT apparatus 140. Broadband source 124 directs light through coupler 38 to probe 46 for obtaining sampled scans of an intraoral feature or other subject. Scanning components that are part of probe 46 direct light from broadband illumination source 124 toward a plurality of points along the intraoral feature to perform the B-scan and C-scan. Low-coherence light from a broadband source 124 is directed through coupler 38 to probe 46 on sample arm 40 and to a reference arm 42. The interference pattern that is generated is measured for a set of randomly distributed frequencies at spectrometer 130. The light goes through a light dispersion optic 20 such as a grating, which provides dispersion of the light. Lens L2 optics then direct this light to a detection array 132. Detection array 132 can be a CCD (charge-coupled device) array or other sensor in the spectrometer that senses the selected wavelengths or wave-numbers. A processor 136, in signal communication with broadband source 124, spectrometer 130 and scanner then provides the logic and control circuitry for random or pseudo-random sampling, compressive sensing computation, image reconstruction, and display. If a swept-source (SS) OCT system is used, the light source can be a frequency-swept tuned laser 50 with a photodetector 60 used in place of the spectrometer, as described in FIGS. 6A and 6B.

Algorithms and utilities for processing sparse-sampled data are well-known to those skilled in the signal processing arts.

Consistent with an embodiment of the present invention, a computer program utilizes stored instructions that perform on image data that is accessed from an electronic memory. As can be appreciated by those skilled in the image processing arts, a computer program for operating the imaging system in an embodiment of the present disclosure can be utilized by a suitable, general-purpose computer system operating as CPU 70 as described herein, such as a personal computer or workstation. However, many other types of computer systems can be used to execute the computer program of the present invention, including an arrangement of networked processors, for example. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present disclosure may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present disclosure may make use of various image manipulation algorithms and processes that are well known. It will be further understood that the computer program product embodiment of the present disclosure may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present disclosure, are not specifically shown or described herein and may be selected from such algorithms, systems, hardware, components and elements known in the art.

Certain exemplary method and/or apparatus embodiments according to the application can provide virtual definition of the base of a dental virtual model. Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by at least the following claims.

The invention claimed is:

1. A method for acquiring image data comprising:
   obtaining, for an intraoral feature, optical coherence tomography (OCT) data in three orthogonal scanning dimensions, wherein at least two dimensions are pseudo-randomly or randomly sampled, wherein one pseudo-randomly or randomly sampled dimension is pseudo-randomly or randomly sampled while scanning along a scan line;
   reconstructing an image volume of the intraoral feature using compressive sensing wherein data density of the reconstructed image volume is larger than that of the obtained OCT data in the at least two dimensions or according to a corresponding transform; and
   rendering the reconstructed image volume for display;
   wherein obtaining the OCT data in three orthogonal scanning dimensions comprises obtaining at each of a number of scan positions along the scan line, an OCT scan comprising a set of multiple light frequencies or wavelengths wherein the light frequencies or wavelengths are randomly or pseudo-randomly spaced.

2. A method for acquiring intraoral volume image data comprising:
   obtaining, along each of a number of scan rows across a surface of a sample, a plurality of optical coherence tomography (OCT) scans, wherein a distance between the OCT scans varies randomly or pseudo-randomly along the scan row;
   reconstructing the intraoral volume using compressive sensing wherein data density of the reconstructed image volume is larger than that of the obtained OCT scans along the row; and
   rendering the reconstructed image volume for display;
   wherein the sample is a tooth, and wherein obtaining, at each of the plurality of OCT scans along the scan rows, comprises an OCT scan comprising a set of multiple light frequencies or wavelengths, wherein the light frequencies or wavelengths are randomly or pseudo-randomly spaced.

3. A method for acquiring intraoral volume image data comprising:
   scanning each row of a sample surface by:
   obtaining, at each of a number of scan positions along the row, an OCT scan comprising of a set of multiple light frequencies or wavelengths wherein the light frequencies or wavelengths are randomly or pseudo-randomly spaced;
   processing each obtained OCT scan using compressive sensing wherein data density of the processed OCT scan is larger than that of the obtained OCT scan;
   combining the processed OCT scans to generate an intraoral volume; and
   rendering the generated intraoral volume for display.

4. The method of claim 3 wherein the randomized or pseudo-randomized set of frequencies or wavelengths are selected using a spectrometer.

5. The method of claim 3 wherein the randomized or pseudo-randomized set of frequencies or wavelengths are generated from a frequency-swept light source.

6. The method of claim 3 wherein using compressive sensing comprises performing minimization computation on each obtained OCT scan.

7. The method of claim 3 wherein distance between the obtained OCT scans also varies randomly or pseudo-randomly along the row, and further comprising processing the generated intraoral volume using compressive sensing to reconstruct the intraoral volume wherein data density of the reconstructed intraoral volume is larger than that of the obtained OCT scans along the row.

8. The method of claim 7 wherein spacing between rows also varies randomly or pseudo-randomly across the sample surface, and the number of rows of the reconstructed intraoral volume is also larger than that of the obtained OCT scans.

9. An apparatus for acquiring volume image data from a tooth, the apparatus comprising:
   a) a broadband illumination source that generates short coherence length light;
   b) a scanner that directs light from the broadband illumination source toward each of a number of points along the tooth;
   c) an interferometer that combines light returned from the scanner with a reference light from the illumination source;
   d) a sensor that is actuable to sense the combined light from the interferometer;
   e) a processor that controls the scanner, illumination source, and sensor to acquire, at said each of the number of points along the tooth, an OCT scan comprising a set of multiple light frequencies or wavelengths, wherein the light frequencies or wavelengths are randomly or pseudo-randomly sampled among the set, and executes a compressive sensing sequence for reconstructing the volume image of the tooth, wherein data density of the reconstructed volume image is larger than that of the acquired data; and
   f) a display in signal communication with the processor for display of the reconstructed volume image.

10. The apparatus of claim 9 wherein the broadband illumination source is a superluminescent diode.

11. The apparatus of claim 9 wherein the broadband illumination source comprises a spatial light modulator.

12. The apparatus of claim 9 wherein the sensor comprises a spectrometer.

13. The apparatus of claim 9 wherein distance between the obtained OCT scans also varies randomly or pseudo-randomly along each scan row.

14. The apparatus of claim 9 wherein the randomly or pseudo-randomly sampled data are acquired in the spatial domain at said each of the number of points along the tooth.

15. The apparatus of claim 9 wherein the reconstructed volume image is displayed after segmentation.

16. The apparatus of claim 9 wherein the reconstructed volume image is displayed after rendering.

17. A method for acquiring intraoral volume image data comprising:
   obtaining, for an intraoral feature, optical coherence tomography (OCT) data in three orthogonal scanning dimensions, wherein the three orthogonal scanning dimensions are pseudo-randomly or randomly sampled;
   applying an interpolation to supplement the OCT scan data with additional computed values for areas between OCT scans; and
   generating the intraoral volume image according to both the measured OCT scans and the additional computed values from interpolation.

18. The method of claim 17 wherein the interpolation is a bilinear interpolation.

19. The method of claim 17 wherein the interpolation is a trilinear interpolation.

20. The method of claim 17 wherein the intraoral feature is a tooth.

* * * * *